United States Patent [19]

Barer et al.

[11] Patent Number: 4,525,362

[45] Date of Patent: Jun. 25, 1985

[54] MOSQUITO DEVELOPMENT INHIBITOR EMPLOYING SUBSTITUTED PHENOLS

[76] Inventors: Sol J. Barer, 130 Tillotson Rd., Fanwood, N.J. 07023; Henry A. Terwedow, Jr., 317 Hill Ave., Glen Ellyn, Ill. 60137

[21] Appl. No.: 583,791

[22] Filed: Mar. 1, 1984

Related U.S. Application Data

[63] Continuation of Ser. No. 310,206, Oct. 9, 1981, abandoned, which is a continuation-in-part of Ser. No. 276,101, Jun. 22, 1981, abandoned, which is a continuation of Ser. No. 208,230, Nov. 19, 1980, abandoned.

[51] Int. Cl.$^3$ .................... A01N 31/00; A01N 31/08
[52] U.S. Cl. .................................. 514/712; 514/734; 514/736
[58] Field of Search ................................. 424/346, 337

[56] References Cited

U.S. PATENT DOCUMENTS

| | | | |
|---|---|---|---|
| 3,839,586 | 10/1974 | Ludvik | 424/346 |
| 3,920,846 | 11/1975 | Hanauye et al. | 424/346 |
| 3,946,047 | 3/1976 | Jurd | 424/346 |
| 3,973,040 | 8/1976 | Jurd | 424/346 |
| 4,082,814 | 4/1978 | Jurd | 424/346 |
| 4,219,570 | 8/1980 | Inazuka et al. | 424/346 |

*Primary Examiner*—Allen J. Robinson
*Attorney, Agent, or Firm*—Scully, Scott, Murphy and Presser

[57] ABSTRACT

Selected substituted phenols may be usefully employed as mosquito development inhibitors.

5 Claims, No Drawings

MOSQUITO DEVELOPMENT INHIBITOR EMPLOYING SUBSTITUTED PHENOLS

CROSS-REFERENCE TO RELATED APPLICATION

This is a continuation of Ser. No. 310,206, filed Oct. 9, 1981, now abandoned, which is a continuation-in-part of application Ser. No. 276,101, filed June 22, 1981, now abandoned, which is a continuation of application Ser. No. 208,230, filed Nov. 19, 1980, now abandoned.

BACKGROUND OF THE INVENTION

1. Field of the Invention

This invention relates to controlling mosquito metamorphosis. More particularly, it relates to the use of organic compounds which prevent or inhibit the growth of mosquito larvae into adult insects. This invention especially relates to the use of phenolic derivatives as mosquito development inhibitors.

2. Description of the Prior Art

There are a variety of techniques for controlling insect populations. In one common method, an insecticide, typically a synthetic organic compound, is applied to the insects or their habitat. This particular method often has undesirable side-effects since the insecticide may cause harm to humans, animals and useful insects, such as bees. Some organochlorine and organophosphorus compounds proved very effective and provided an initial high degree of safety to vertebrates but later proved potentially toxic to vertebrates because they attacked biological processes vertebrates shared with anthropods. Further, these compounds were often very stable, i.e., they were not biodegradable and thus tended to persist in the environment and in animal tissues. In addition, some insects developed a tolerance to these compounds to the point that the insecticides were of limited effectiveness. In view of these drawbacks, alternate means of insect control have been sought.

Effective control of insects has more recently been obtained by utilizing chemical compounds which act as anti-procreants. When one type of anti-procreant is administered, the insects become sexually sterile so that when mated with fertile insects, the eggs which are laid do not yield any progeny. Other anti-procreants produce the result that the female species does not lay any eggs and consequently no progeny result. These compounds are known, respectively, as chemosterilants and oviposition inhibitors.

Another approach to insect control, which is environmentally acceptable, exploits the hormones by which an insect regulates its growth and development. Two of the major insect hormones are the juvenile hormones (JH) and molting hormones (MH) or ecdysones. These hormones regulate insect growth and maturation. In the growing process, the insect larvae must molt—shed their rigid cuticles and replace them with new ones. Larval molting requires both JH and MH materials. Larvae die because of abnormal development when JH is present at the incorrect time. JH materials have been developed more readily than the ecdysones since the latter are steroids whose complexity often makes synthesis difficult and costly.

Application of JH insecticides is somewhat restricted because they are effective only at certain specific stages of insect life—hence timing is extremely important. A major problem in use of JH analogs is their ineffectiveness early in larval life. When the larval form is the pest, as for example caterpillars of moth species, they may cause considerable damage before they die. Thus, in the present state of the art, hormonal insecticides are most suited for use against light manifestations for which the amount of damage is economically tolerable, or against adult pests, such as mosquitos or flies. Compounds that inhibit the synthesis or action of these compounds so as to prevent molting at all stages of development, including the earliest would be most useful in this service.

These so-called "third generation pesticides" control insect population by inhibiting or preventing insect larvae or pupae from reaching the adult stage of insect development. Such compounds are referred to in the art as juvenile hormone (JH) mimics or insect development inhibitors. These agents do not kill the larvae, but rather prevent the growth thereof beyond the larval or pupal stage. Consequently, the number of adults is substantially reduced. The mimics actually cause several different situations, all of which result in controlling insect population. First of all, most of the treated larvae do not reach adulthood. Thus, the larvae survive for a period of time (possibly an entire growing season) as either larvae or pupae, and then die. During that period the larvae are, of course, very susceptible to predation and injurious climatic conditions. Furthermore, they are themselves incapable of reproduction, thus reducing the insect population for the next growing season. Secondly, some of the treated larvae may develop to various stages of adulthood. For example, the adult insect may only partially eclose, i.e., emerge from the larval or pupal shell. On the other hand, full eclosion may occur but the adult insect is either malformed or dead. In either case, the population of adult insects is substantially reduced.

The growth-inhibiting compounds have many advantages over insecticides and the like. First, the growth-inhibitors do not yield unwanted ecological side effects. Secondly, since the growth inhibitors act as juvenile hormone mimics, the insects do not develop a tolerance to the compounds. Thus, the compounds will not eventually become ineffective. Third, the growth inhibiting compounds are not harmful to beneficial insects or mammals because they are quite specific for a particular kind of insect.

It has been reported that some phenol derivatives have biological activity that mimics that of natural insect juvenile hormones and function as insect development inhibitors. Sacher reported that 2,6-di-t-butyl-4(alpha-alpha-dimethylbenzyl)phenol prevents mosquito larvae from metamorphosizing (31 *Mosquito News* (4) 513 (1971)). Schaefer et al. disclosed insect development inhibition for similar phenolic compounds wherein the substituent in the fourth position contained sulfur plus Co or CCl (Proc. 42nd Ann. Conf. Calif. Mosquito Control Assn. 147 (1974)). Schaefer and another co-worker found high JH mimic activity for several esters of dodecadienoic acid and an epoxy-phenoxyoctene (65 *J. Econ. Ent.* (4) 1066 (1972)).

The patent art also discloses specific JH mimics. U.S. Pat. No. 3,839,586 of Ludvik discloses that substituted phenols of the formula

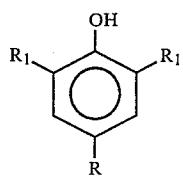

where R is hydrogen, isopropylphenyl or a $C_1$–$C_6$ alkyl, alkoxy or thioalkyl and $R_1$ is tertiary-butyl, tertiary-pentyl or cyclohexyl, prevent mosquito pupae from developing properly when applied to the larvae. These 2,6 substituted phenols include the compound evaluated by Sacher. Ludvik found, however, that not all 2,6 substituted phenols exhibit this inhibition. Thus 2,6-di-isoamyl phenol, 2,6-di-t-butyl-4-chlorophenol and 2,6-di(methylnonyl)phenol show no such activity.

Other phenolic compounds similar to those of Ludvik were also found to exhibit mosquito development inhibition. U.S. Pat. No. 3,920,846 of Hanauye et al discloses a series of t-butyl-benzyl phenols while U.S. Pat. Nos. 3,973,040 and 4,082,814 of Jurd disclose a number of poly-t-butyl-cinnamyl phenols which function as JH mimics.

U.S. Pat. No. 3,920,844 of Barer et al (N-haloaminodiarylalkanes and N-haloaminodiarylhaloalkanes), U.S. Pat. No. 3,941,777 of Madsen et al (oximethers of certain aldehydes and ketones) and U.S. Pat. No. 3,941,842 of Metcalf et al (p,p'-disubstituted alpha-trichloromethylbenzylanilines) all disclose specific organic compounds which exhibit JH mimic activity when applied to mosquito larvae thereby preventing proper development to the adult stage.

It is apparent from the prior art that some organic compounds, particularly substituted phenols, function as mosquito development inhibitors while some do not. It appears that this activity cannot be predicted but can only be determined from actual use.

It is an object of this invention to provide a method of inhibiting mosquito development utilizing organic compounds not employed previously for this purpose.

It is another object of this invention to provide a method of inhibiting mosquito development utilizing organic chemicals available commercially but not employed for this purpose heretofore.

It is a further object of this invention to provide a method of inhibiting mosquito development utilizing substituted phenols which have not been employed for this purpose heretofore.

SUMMARY OF THE INVENTION

In accordance with the present invention, it has been found that a number of commercially available, substituted phenols will function as insect development inhibitors when applied to mosquito larvae. More particularly this invention is directed to a method of inhibiting the development of mosquito larvae to the adult stage which comprises applying to the larvae an amount effective to inhibit development of the mosquito larvae to the adult stage of a compound having the formula

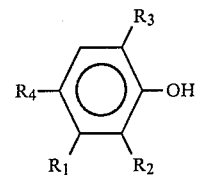

wherein $R_1$ is hydrogen or methyl, $R_2$ and $R_3$ are the same or different and are hydrogen, tertiary-butyl or styryl, $R_4$ is hydrogen, methyl, nonyl,

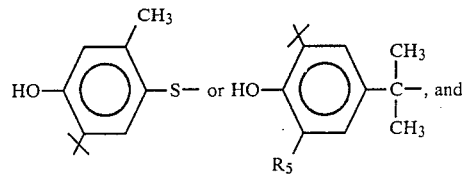

$R_5$ is hydrogen or tertiary-butyl with the provisos that $R_1$ or $R_2$ is always hydrogen and that when $R_4$ is hydrogen, methyl or nonyl, each of $R_2$ and $R_3$ is other than hydrogen.

The useful compounds employed herein may also be described using the above formula but substituting the following for the above provisos: that $R_1$ or $R_2$ is always hydrogen and that no more than two of $R_1$, $R_2$, $R_3$ and $R_4$ are hydrogen.

DESCRIPTION OF THE PREFERRED EMBODIMENTS

The present invention relates to particular substituted phenols which function as mosquito JH mimics in that they inhibit the development of mosquitoes in the pupal stage so that most, if not all, of the larvae do not reach adulthood. In general, these compounds have no apparent effect on the larvae and do not interfere with the actual transformation to the pupal stage. The resultant pupae, however, remain white, fail to develop normally, and die before the emergence of the adult stage mosquitoes. The compounds of this invention are not larvicidal in their activity but function as insect development inhibitors.

The phenolic compounds employed in the present invention are all commercially available but they have not been used heretofore as a mosquito pesticide. However, in view of the findings in the prior art of the specificity of phenolic compounds when employed as insect development inhibitors, this is not surprising.

The compounds usefully employed in the process of the present invention are listed below together with the trade names for the commercial products of which the compound constitutes the active ingredient:

| | |
|---|---|
| 2,-di-styrylphenol | (Wing Stay 5) |
| 2,6-di-styryl-4-methyl phenol (also called 2,6-di-styryl-p-cresol) | (Naugard 431) |
| 2,6-di-tertiary-butyl-4 nonylphenol | (Uvinox 1494) |
| 4,4'-thio-bis (3-methyl-6-tertiary butyl phenol) (also called 4,4'-thio-bis-6-tertiary butyl-m-cresol) | (Santanox R) |
| poly-tertiary-butyl-4,4'-dihydroxydiphenyldimethylmethane (also called poly-tertiary butyl-bisphenol A) | (Goodrite 3112) |

Although all five of these compounds provide effective control of mosquitoes, Wing Stay 5, Uvinox 1494 and Santanox R are more effective in the sense that they are more effective at the same concentrations or are equally effective at lower concentrations than the other two.

These compounds may be represented by the formula

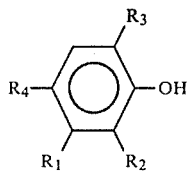

wherein $R_1$ is hydrogen or methyl, $R_2$ and $R_3$ are the same or different and are hydrogen, tertiary butyl or styryl, $R_4$ is hydrogen, methyl, nonyl,

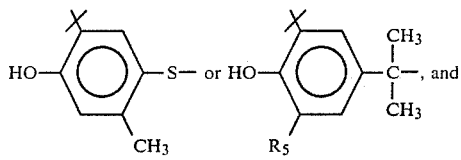

$R_5$ is hydrogen or teriary butyl with the provisos that $R_1$ or $R_2$ is always hydrogen and that when $R_4$ is hydrogen, methyl or nonyl, each of $R_2$ and $R_3$ is other than hydrogen.

In another manner of describing these compounds the above formula and its substituents are employed but the limitations as to the substituents are described as follows: with the provisos that $R_1$ or $R_2$ is always hydrogen and that no more than two of $R_1$, $R_2$, $R_3$ and $R_4$ are hydrogen.

It is obvious that Goodrite 3112 may contain a mixture of compounds as two, three, or four tertiary butyl groups may be substituted on bisphenol A to provide the 2,2′, the 2,2′,6 or the 2,2′,6,6′ isomers. In the practice of this invention any of these isomers or mixtures of two or more of them may be employed.

Since mosquito larvae develop in water, the process of this invention is most effectively practiced by adding an effective amount of one of the above compounds to the surface of the water habitat of the mosquito larvae. This may be accomplished by any of the procedures well known in the art, such as dispersing the compound over the surface, admixing the compound with an appropriate solid carrier and spreading the mixture over the surface, or spraying a solution or a dispersion of the compound in a liquid carrier onto the water surface.

The quantity of the useful substituted phenol employed in this invention must be an amount which is effective in controlling or inhibiting mosquito larvae development. The concentration of the compound required to achieve mosquito growth inhibition will vary depending on the activity of the selected compound. In any particular case the appropriate amount to be used can readily be determined without an undue amount of experimentation by pilot tests well known to those skilled in the art. In most situations effective control is achieved with concentrations of the phenolic compound which are in the range of 0.01–10.0 ppm, preferably 0.1–5.0 ppm in the aqueous environment of the larvae. Since these growth inhibitors are effective only on mosquito larvae, they have no apparent effect on adult mosquitoes and therefore must be administered to the larvae to achieve the desired growth inhibition. These inhibitors may effectively be applied to mosquito habitats which contain organic pollutants such as decaying animal and/or vegetable matter found in such common mosquito grounds as stagnant ponds and swamps.

Because the compounds of the invention are effective in very minor concentrations, it is preferred that they be dissolved or suspended in what is known in the art as an extending agent or a carrier prior to application to the breeding centers. The solution or suspension increases the bulk, and thus makes is easy to administer small amounts of the compounds to the mosquito breeding area. Solvents appropriate for the purpose should be volatile ones, such as acetone, ethyl ether, ethanol, benzene, xylene, petroleum, naphtha, and the like.

When solid formulations are desired, the extending agents that can be used include tricalcium phosphate, calcium carbonate, diatomaceous earth, talc, wood flour and the like, which are preferably reduced to a particle size of about 5 microns or less. In some instances it may be useful to employ a surface active agent to facilitate dispersion of the active compounds throughout the aqueous habitat of the mosquito larvae. The concentration of the compounds of this invention in such formulations can vary from about 1 to about 98% by weight of the composition and the compositions are usually applied to the aqueous habitat in sufficient quantity to provide a concentration between about 0.01 and about 10 ppm, preferably about 0.1–about 5 ppm.

The following example will serve to illustrate the subject invention.

EXAMPLE

A number of commercially available products whose active ingredients was in each instance a substituted phenol were evaluated as mosquito development inhibitors.

The following products were tested:

| Tradename | Active Ingredient | Name |
|---|---|---|
| Wing Stay 5 | | 2,6-di-styryl-phenol |
| Uvinox 1494 | | 2,6-di-tertiary butyl-4 nonyl-phenol |
| Naugard 431 | | 2,6-di-styryl-4-methylphenol |

-continued

| Tradename | Active Ingredient | Name |
|---|---|---|
| Santanox R | 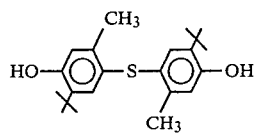 | 4,4'-thio-bis (3-methyl-6-tertiary butyl phenol) |
| Goodrite 3112 | 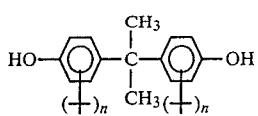 | poly-tertiary butyl-4,4'-dihydroxy-diphenyldimethylmethane. |

The products were tested for insect growth regulant activity in a bioassay using *Culex pipiens pipiens*. Twenty-five mid-third instar larvae were counted into 200 ml. of tap water. To this was added 0.1 ml. of ethanol containing the appropriate amount of test material. Five replicates were run for each concentration level being evaluated. Food was added in small amounts until the majority of mosquitoes had reached pupation. Ethanol controls were run concurrently. All mortality occurred in early to medial pupation.

The results obtained are presented in the following table.

PERCENT MORTALITY OF *C. PIPIENS PIPIENS*
(Mean of five replicates of 25-3rd instar.)

| Concentration of antioxidant in tap water, ppm. | Wing Stay 5 | Uvinox 1494 | Naugard 431 | Santanox R | Goodrite 3112 |
|---|---|---|---|---|---|
| 5.0 | 99.2 | 100 | 99.2 | 100 | 100 |
| 2.5 | 98.4 | 100 | 96.8 | 99.1 | 96.8 |
| 1.0 | 97.6 | 100 | 47.2 | 97.6 | 71.2 |
| 0.5 | 80.8 | 84.8 | 28.0 | 89.6 | 9.6 |

PERCENT MORTALITY OF *C. PIPIENS PIPIENS*
(Mean of five replicates of 25-3rd instar.)

| Concentration of antioxidant in tap water, ppm. | Wing Stay 5 | Uvinox 1494 | Naugard 431 | Santanox R | Goodrite 3112 |
|---|---|---|---|---|---|
| 0.25 | 76.0 | 76.8 | 4.8 | 36.0 | 5.6 |
| Control | 6.4 | 4.8 | 2.4 | 8.8 | 10.4 |

What is claimed is:

1. A method of inhibiting the development of mosquito larvae to the adult stage which comprises applying to the larvae an amount effective to inhibit development of the mosquito larvae to the adult stage of a compound having the formula

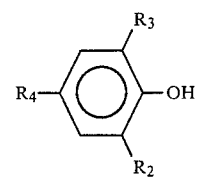

wherein $R_2$ and $R_3$ are styryl, and $R_4$ is hydrogen, methyl or nonyl.

2. A method according to claim 1 wherein $R_2$ and $R_3$ are styryl and $R_4$ is hydrogen.

3. A method according to claim 1 wherein $R_2$ and $R_3$ are styryl and $R_4$ is methyl.

4. A method of inhibiting the development of mosquito larvae to the adult stage which comprises applying to the larvae an amount of 4,4'-thio-bis(3-methyl-6-tertiary butyl phenol) effective to inhibit development of the mosquito larvae to the adult stage.

5. A method of inhibiting the development of mosquito larvae to the adult stage which comprises applying to the larvae an amount of the $2,2^1$-di-tertiary-butyl isomer, the $2,2^1,6$-tritertiary-butyl isomer, the $2,2^1,6,6^1$-tetra-tertiary-butyl 4,4'-dihydroxydiphenyl-dimethylmethane or mixtures thereof effective to inhibit development of the mosquito larvae to the adult stage.

* * * * *